United States Patent [19]

Isshiki et al.

[11] Patent Number: 4,843,170

[45] Date of Patent: Jun. 27, 1989

[54] PROCESS FOR PRODUCING VINYL ACETATE

[75] Inventors: Tomiya Isshiki, Tokyo; Yasuhiko Kijima; Akira Ito, both of Matsudo; Kenji Ishii, Tokyo, all of Japan

[73] Assignee: Mitsubishi Gas Chemical Company, Inc., Tokyo, Japan

[21] Appl. No.: 466,653

[22] Filed: Feb. 15, 1983

Related U.S. Application Data

[63] Continuation of Ser. No. 197,137, Oct. 15, 1980, abandoned.

[30] Foreign Application Priority Data

Oct. 18, 1979 [JP] Japan .................. 54-134358

[51] Int. Cl.⁴ .................. C07C 69/15; C07C 67/297
[52] U.S. Cl. .................. 560/261; 260/549; 560/238; 560/240; 560/248; 560/232; 562/607
[58] Field of Search ........... 560/261, 232, 238, 240; 260/549

[56] References Cited

U.S. PATENT DOCUMENTS

| | | | |
|---|---|---|---|
| 2,251,983 | 8/1941 | Chitwood | 560/261 |
| 2,607,787 | 8/1952 | Mason | 260/549 |
| 2,723,287 | 11/1955 | Copenhaver | 560/240 |
| 2,727,902 | 12/1955 | Reppe et al. | . |
| 2,859,241 | 11/1955 | Schnizer | 560/261 |
| 2,860,159 | 11/1958 | Sharp et al. | 560/261 |
| 4,002,677 | 1/1977 | Naglieri et al. | 260/549 |
| 4,046,807 | 9/1977 | Kuckertz | 260/549 |

FOREIGN PATENT DOCUMENTS 2856791 12/1979 Fed. Rep. of Germany .
39-25031 11/1964 Japan .................. 260/232

OTHER PUBLICATIONS

Man et al., (Man), *Journal of the American Chemical Society*, vol. 72, (1950), pp. 847–848.
Bull. Chem. Soc. Japan, 52(2), 479–482 (1979).
Merck Index, 9th Ed., p. 501 (1976)—Compound No. 3751.

*Primary Examiner*—Vivian Garner
*Attorney, Agent, or Firm*—Fleit, Jacobson, Cohn & Price

[57] ABSTRACT

A process is disclosed for producing vinyl acetate from methanol, carbon monoxide and hydrogen which comprises the following five steps:

(a) methanol is hydrocarbonylated in a hydrocarbonylation zone to produce ethanol, acetaldehyde, methyl acetate and dimethylacetal, and the products are separated in a separation zone;

(b) methyl acetate is carbonylated in a carbonylation zone to produce acetic anhydride;

(c) the acetaldehyde and dimethylacetal produced in the step (a) and the acetic anhydride produced in the step (b) are converted to ethylidene diacetate and methyl acetate; (d) the ethylidene diacetate produced in the step (c) is thermally decomposed to vinyl acetate and acetic acid, and the products are separated in a separation zone; and (e) the methyl acetate produced and separated in the step (a), (c) or (d) is supplied to the carbonylation step (b).

8 Claims, 1 Drawing Sheet

Fig. 1

PROCESS FOR PRODUCING VINYL ACETATE

This is a continuation of application Ser. No. 197,137 filed Oct. 15, 1980, now abandoned.

BACKGROUND OF THE INVENTION:

1. Field of the Invention:

This invention relates to the production of vinyl acetate, and more particularly, to the production of vinyl acetate integrated in a complex process that achieves simultaneous production of vinyl acetate.

2. Description of the Prior Art:

In the wake of "oil crisis", the price of crude oil increased greatly, and as a result, the prices of petrochemical building blocks such as ethylene and propylene soared. In consequence, ethylene and propylene derivatives are losing the competitive power, and people in the industry even see the necessity of manufacturing some derivatives from other sources by processes other than the conventional ones. In the development of technology for producing ethylene and propylene derivatives from sources other than crude oil by unconventional methods, an important role is expected to be played by natural gases which are $C_1$ compounds per se, and other $C_1$ compounds such as a synthesis gas (a mixture of carbon monoxide and hydrogen), and carbon dioxide produced by gasification of asphalt and solid fossil fuels such as coal, as well as methanol derived from these gases. Utilization of these $C_1$ compounds is one of the top-priority objects that must be achieved as soon as possible to meet the demand for less dependency on petroleum and use of more varigated sources of ethylene and propylene derivatives.

Ethanol is known as an industrial chemical and basically it has been manufactured by fermentation of natural products such as molasses or by hydration of ethylene in the presence of an acid catalyst such as phosphoric acid. As already mentioned, ethylene is one of the petrochemicals which are getting more and more expensive. Coal and natural gas are two ample natural resources, and both of them can be converted to a synthesis gas ($CO+H_2$) from which methanol can be produced. The methanol further reacts with carbon monoxide and hydrogen under appropriate conditions to form ethanol, acetaldehyde, dimethyl acetal and methyl acetate [see, for example, Japanese Patent Publications Nos. 15692/66, 2525/73, Japanese Patent Public Disclosures Nos. 149213/76, 136110/77, 136111/77, 133914/76, Bull, Chem. Soc., Jpn., 52 (2), 479–482 (1979)].

Like ethanol, vinyl acetate is a well known industrial chemical. It is one of the oldest vinyl monomers and polyvinyl acetate and PVA (polyvinyl alcohol) are useful synthetic polymers, so there are many different methods to produce it on an industrial scale. In old days, vinyl acetate was typically synthesized from acetylene, and these days, the acetylene process is being displaced by a more advantageous ethylene process. The first concept of direct synthesis of vinyl acetate from ethylene used a palladium chloride catalyst or sodium acetate in the reaction system. Alternative methods were proposed wherein vinyl acetate and acetic acid were produced from acetaldehyde and acetic anhydride either directly or through ethylidene diacetate (1,1-diacetoxyethane) [see, for example, Hydrocarbon Process, 44 (11) 287 (1965), British Pat. No. 1,112,555, U.S. Pat. Nos. 2,021,698, 2,425,389 and 2,860,159]. In these methods, acetaldehyde and acetic anhydride are reacted directly to form vinyl acetate and acetic acid or they first react to form ethylidene diacetate which is then thermally decomposed to vinyl acetate and acetic acid.

Acetic anhydride used as one of the two starting materials in these methods has been commercially produced by the Wacker process wherein acetone or acetic acid is thermally decomposed to ketene which is then reacted with acetic acid to produce acetic anhydride. Methods have been proposed recently that produce acetic anhydride directly from methyl acetate and carbon monoxide by reacting them in the presence of a carbonylation catalyst and a halide (see, for example, Japanese Patent Publication No. 3926/77, Japanese Patent Public Disclosures Nos. 65709/76 and 59214/79).

Acetaldehyde, the other material for the production of vinyl acetate by thermal decomposition is an industrial chemical that is commercially produced mainly by direct oxidation of ethylene or light hydrocarbons. In other words, like ethanol, vinyl acetate or acetic anhydride, acetaldehyde is also supplied to the market as a product produced from petrochemicals whose prices keeps going up. Methods have therefore been proposed to produce $C_2$ compounds directly from a synthesis gas (see, for example, Japanese Patent Public Disclosures Nos. 80806/76 and 80807/76). These methods constitute an attractive process for synthesizing $C_2$ compounds, considering only the starting material. But unfortunately, the process involves a gas-phase reaction using a solid catalyst one component of which is rhodium, so metallic rhodium in the solid catalyst changes to volatile rhodium carbonyl which escapes out of the reaction system until the catalytic activity is lost. This defect is fatal to the process if it is to be performed on an industrial scale, and a considerable time will be necessary to eliminate such defect.

According to more viable methods, $C_2$ compounds such as acetaldehyde and ethanol are produced from methanol and synthesis gas, as taught in, say, Japanese Patent No. 2525/73, Japanese Patent Public Disclosures Nos. 149213/76, 136110/77, 136111/77, and Bull, Chem. Soc. Jpn., 52 (2), 479–482 (1979). The reactions that occur in these methods for producing ethanol, acetaldehyde, methyl acetate and dimethyl acetal are schematically represented by the following formulae:

(1) $CH_3OH + CO + 2H_2 \rightarrow CH_3CH_2OH + H_2O$
(2) $CH_3OH + CO + H_2 \rightarrow CH_3CHO + H_2O$
(3) $2CH_3OH + CO \rightarrow CH_3COOCH_3 + H_2O$
(4) $3CH_3OH + CO + H_2 \rightarrow CH_3CH(OCH_3)_2 + 2H_2O$ As understood from these reaction formulae, the conventional methods for producing ethanol and acetaldehyde by hydrocarbonylation of methanol is disadvantageous in that it produces a great amount of methyl acetate or dimethyl acetal other than the desired products. Attempts have been made to improve the catalyst or increase the yield of ethanol and acetaldehyde by recycling the by-products, but none of them have proved completely satisfactory for practical purposes.

SUMMARY OF THE INVENTION

Therefore, one object of this invention is to achieve effective use of ethanol and acetaldehyde produced from methanol and synthesis gas, as well as methyl acetate and dimethylacetal by integrating them in an industrial process as starting materials.

Another object of this invention is to produce vinyl acetate from materials that are not derived from ethylene or other petrochemicals.

These objects of this invention are achieved by integrating the step of hydrocarbonylation and, the steps for producing acetic anhydride and vinyl acetate into a systematic process.

Therefore, in step (a) of the process of this invention, methanol is hydrocarbonylated to $C_2$ compounds such as ethanol, acetaldehyde, methyl acetate and dimethylacetal, and the reaction mixture containing these compounds is then freed of ethanol, acetaldehyde, methyl acetate and dimethylacetal; concurrently, in step (b), methyl acetate is carbonylated to acetic anhydride which is then freed from the reaction mixture; the mixture of acetaldehyde and dimethylacetal separated in step (a) is reacted with acetic anhydride to form a vinyl acetate precursor ethylidene diacetate (hereunder referred to as ED) and methyl acetate (step (c)), or vinyl acetate, acetic acid and methyl acetate are produced directly and simultaneously (step (c) combined with step (d)); both the methyl acetate produced in the step (c) or the combination of steps (c) and (d) and the methyl acetate produced in the step (a) are carbonylated to acetic anhydride. The above cycle is repeated. When ED is synthesized as a precursor, it is thermally decomposed (step (d)) to vinyl acetate and acetic acid. In summary, this invention accomplishes simultaneous production of vinyl acetate, acetic acid and ethanol from methanol, carbon monoxide and hydrogen.

This invention provides a complex, recycling process for producing vinyl acetate from methanol, carbon monoxide and hydrogen which comprises the following five steps:

(a) methanol is hydrocarbonylated in a hydrocarbonylation zone to produce ethanol, acetaldehyde, methyl acetate and dimethylacetal, and the products are separated in a separation zone;

(b) methylacetate is carbonylated in a carbonylation zone to produce acetic anhydride;

(c) the acetaldehyde and dimethylacetal produced in the step (a) and the acetic anhydride produced in the step (b) are converted to ethylidene diacetate and methyl acetate;

(d) the ethylidene diacetate produced in the step (c) is thermally decomposed to vinyl acetate and acetic acid, and the products are separated in a separation zone; and (e) the methyl acetate produced and separated in the steps (a), (c) or (d) is supplied to the carbonylation step (b).

DETAILED DESCRIPTION OF THE INVENTION:

The respective steps of this invention are hereunder described in detail.

Step (a):

Hydrocarbonylation of methanol with carbon monoxide and hydrogen is preferably performed in the hydrocarbonylation zone in the presence of a catalyst, say, a metal belonging to the group VIII of the periodic table, such as cobalt or ruthenium described in Japanese Patent Publications Nos. 15692/66, 2525/73, Japanese Patent Public Disclosures Nos. 149213/76, 136110/77, 136111/77, 133914/76, and Bull. Chem. Soc. Jpn., 52 (2), 479–482 (1979). A cobalt catalyst is particularly preferred. The metal catalyst used in this invention may be in any valence state having a desired atomic valency including zero. Illustrative cobalt metal catalysts include metallic cobalt, cobalt acetylacetonate, cobalt hydroxide, cobalt carbonate, cobalt formate, cobalt acetate, cobalt propionate, cobalt naphthenate, cobalt stearate, cobalt chloride, cobalt bromide, cobalt iodide, dicobalt octacarbonyl, tetracobalt dodecacarbonyl, hydridotetracarbonylcobalt, and dicobalt hexacarbonyl bis(tri-n-butylphosphine). The amount of the metal catalyst used is not critical, but usually, $10^{-6}$ to 0.5 mols, preferably $10^{-5}$ to 0.05 mols, more preferably from $10^{-4}$ to 0.025 mols, of the metal catalyst is used per liter of the reaction medium on the basis of metal atom.

The hydrocarbonylation may be carried out with advantage using a halogen or a halide as a secondary component. Preferred halides are bromides or iodides or mixtures thereof. Illustrative halides are alkyl halides such as methyl iodide, acid halogenides such as acetyl iodide, hydrogen halides such as hydrogen iodide, and organic halide salts and inorganic halides such as ammonium iodide and tetramethyl ammonium iodide salt. Iodines ($I_2$), bromine ($Br_2$) and inorganic halides such as alkali metal and alkaline earth metal halides are particularly preferred. Iodine ($I_2$) and bromine ($Br_2$) are also effective and they immediately react with the reactants to form an iodide or bromide. Typical examples of these inorganic halides are LiI, KI, NaI, $CaI_2$, $HIO_3$, LiBr, KBr, NaBr, $CaBr_2$, and $HBrO_3$. These halogen or halides are added to the reaction system in an amount of from $10^{-6}$ to 0.25 mols, preferably from $10^{-5}$ to 0.05 mols per liter of the reaction medium on the basis of halogen atom.

The hydrocarbonylation reaction of this invention may be adequately achieved in the presence of a catalyst system consisting of a carbonylation catalyst and a halide secondary component, but an organic reaction accelerator may be used in combination with the catalyst system. Advantageous organic reaction accelerators are organic nitrogen, phosphorus, antimony, arsenic and bismuth compounds. Part of these compounds are represented by the following formula:

(wherein M is N, P, Sb, As or Bi; $R_1$, $R_2$ and $R_3$ which may be the same or different are each hydrogen, or an alkyl, cycloalkyl or aryl group preferably having not more than 10 carbon atoms). The following are examples of the organic reaction accelerator which are given here not for limiting purposes but for illustrative purposes only: amines such as monomethylamine, dimethylamine, trimethylamine, dimethylethylamine, diethylamine, tri-iso-propylamine, tri-n-propylamine, tri-n-butylamine, tri-tert-butylamine, aniline, dimethylaniline, and diethylaniline; phosphines such as tri-n-propylphosphine, tri-iso-propylphosphine, tri-n-butylphosphine, tri-tert-butylphosphine, tricyclohexylphosphine, ethylene bis(diphenylphosphine) and triphenylphosphine; arsines such as trimethylarsine, triethylarsine, tricyclohexylarsine, triphenylarsine, phenyl-di-iso-propylarsine, diphenylarsine, bis(diphenylarsino) ethane, and bis(di-iso-propylarsino)hexane; stibines such as tri-iso-propylstibine, ethyl-di-iso-propylstibine, triphenylstibine, tri(o-tolyl)-stibine, phenyldiamylstibine, tris(diethylaminomethyl)stibine and bis(diethylstibino)pentane; and triphenylbismuth, trimethylbismuth, tricyclohexylbismuth and triethylbismuth.

Other organic nitrogen compounds which may or may not contain oxygen or phosphorus atom are used with advantage as the organic reaction accelerator. Non-limiting examples of these compounds include heterocyclic compounds such as pyrrole, pyrrolidine, piperidine, pyrimidine, picolines, pyrazine and N-$C_{1-5}$ lower alkyl substituted derivatives thereof such as N-methylpyrrolidine, benzotriazole, piperazine, N-methyl piperazine, N-ethylpiperazine, 2-methyl-N-methylpiperazine, 2,2-dipyridyl, methyl-substituted 2,2-dipyridyl, 1,4-diazabicyclo(2,2,2)octane, methyl-substituted 1,4-diazabicyclo(2,2,2)octane, purine, 2-aminopyridine, 1,10-phenanthroline, methyl-substituted 1,10-phenanthroline, 2-(dimethylamino)pyridine, 2-(dimethylamino)-6-methoxyquinoline, 7-chloro-1,10-phenanthroline, 4-triethylsilyl-2,2'-dipyridyl, 5-(thiabenzyl)-1,10-phenanthroline, pyridine, 2,4-dimethyl pyridine, 2,6-dimethyl pyridine, 2,4,6-trimethylpyridine, and imidazole; diamines, such as N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylethylenediamine, and N,N,N',N'-tetra-iso-butylmethylenediamine; and nitriles, such as acetonitrile, propionitrile, adiponitrile, and benzonitrile.

The organic compounds having oxygen or phosphorus atom and nitrogen atom include hydroxyl or carboxyl-substituted compounds of the above mentioned organic nitrogen compounds, such as 2-hydroxypyridine, methyl-substituted 2-hydroxypyridine, picolinic acid, methyl-substituted picolinic acid, 2,5-dicarboxypiperazine, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, salts of ethylenediaminetetraacetic acid, such as tetramethyl ester of ethylenediaminetetraacetic acid, ammonium salts like ammonium acetate; carboxylic amides, such as acetamide, acetanilide, N,N-dimethylacetamide, and N-methyl-N-phenylacetamide; amino acids, such as N,N-dimethylglycine, and N,N-diethylglycine; 1-methyl-2-pyrrolidinone, 4-methyl-morpholine, N,N,N',N'-tetramethylurea, N-methyliminodiacetic acid, nitrilotriacetic acid, and N-methyl iminodiacetic acid; and phosphine iminium salts such as triphenylphosphine iminium chloride. Organic reaction accelerators having trivalent nitrogen, phosphorus, antimony and bismuth are particularly preferred.

The amount of the organic reaction accelerator used depends on the amount of the metal catalyst used in the reaction zone, but usually, $10^{-6}$ to 0.25 mols, preferably $10^{-5}$ to 0.05 mols of the accelerator per liter of the reaction medium is used.

In the practice of this invention, hydrocarbonylation is performed suitably at a temperature in the range of from 50° to 450° C., preferably from 100° to 350° C., and more preferably from 150° to 300° C. Carbon monoxide and hydrogen preferably have a partial pressure of from 15 to 1000 atm., more preferably from 20 to 800 atm., and most preferably from 25 to 400 atm. A partial pressure may be in the range of from 10 to 1500 atm. Carbon monoxide and hydrogen may be supplied under pressure to the reaction zone either independently or as a mixture. The molar ratio of carbon monoxide to hydrogen is selected from a wide range of 1:100 to 100:1, but a preferred range is from 1:50 to 50:1, and a more preferred range is from 1:10 to 10:1. Good results are obtained when a gas mixture having a CO to $H_2$ ratio close to the stoichiometrical ratio of the two gases used for synthesis of $C_2$ compounds is used, and for this purpose, using a CO to $H_2$ molar ratio between 1:5 and 5:1 is a particularly preferred operation method. Carbon monoxide and hydrogen need not always have high purity and they may contain carbon dioxide, methane, nitrogen, rare gas, water or a trace amount of oxygen. Carbon monoxide and hydrogen of extremely low purity are not preferred because they increase the pressure of the reaction system.

Usually, the effluent from the hydrocarbonylation zone is a mixture of gas and liquid and directed to a high-pressure separation unit for gas-liquid separation. Most of the gas separated is recycled to the reaction zone. The liquid effluent is freed of ethanol/acetaldehyde and methyl acetate/dimethylacetal by a suitable separation technique such as distillation or liquid-liquid separation, and the unreacted methanol, halide component and metallic catalyst component are recovered and recycled to the hydrocarbonylation zone. Likewise, part of the products such as dimethylacetal and methyl acetate may be recycled to the hydrocarbonylation zone. The separation zone usually consists of more than one distillation unit such as a flash distillation column and/or separation column. The distillation unit is typically used at a temperature between 40° and 200° C. and a pressure less than 5 atm. The liquid-liquid separation zone usually consists of more than one liquid-liquid separation unit such as extraction column and/or liquid-liquid separation column. The liquid-liquid separation zone is operated by a method well known to those skilled in the art and is primarily used for separation of methanol and dimethylacetal.

Most of methyl acetate produced in the step (a) is usually supplied as the material for the step (b). Dimethylacetal on the other hand is used as a material for the step (c) after it is separated from methanol and other contaminating substances in the effluent by such a technique as distillation or liquid-liquid separation. Alternatively, the dimethylacetal is hydrolyzed by a known method to methanol and acetaldehyde which is supplied as a material for the step (c). Otherwise, the dimethylacetal may be recycled to the step (a) together with the unreacted methanol. In a desired embodiment, the recently proposed method of producing $C_2$ compounds such as acetaldehyde and ethanol directly from a synthesis gas (see, for example, Japanese Patent Public Disclosures Nos. 80806/76 and 80807/76) may be applied to the hydrocarbonylation zone of the step (a).

Step (b):

In the step (b), acetic anhydride may be produced from the carbonylation zone as a result of carbonylation of methyl acetate with carbon monoxide. The reaction is performed with advantage in the presence of a catalyst. A suitable catalyst is composed of a metal component and halide component, that produces a carbonyl compound in the reaction system (illustrative catalysts are described in, say, Japanese Patent Publication No. 3926/77, Japanese Patent Public Disclosures Nos. 65709/76 and 59214/79). The metal component is based on the use of a metal of group VIII, and a component based on palladium, iridium, rhodium, nickel or cobalt is effective, and one based on palladium, rhodium or nickel is particularly effective. The metal component is used in any suitable form, and some of their examples include: $RhX_3$, $RhX_3 \cdot 3H_2O$, $[RhX(CO)_2]_2$, $Rh_6(CO)_{16}$, $RhX(PPh_3)_3$, $Rh(SnCl_3)(PPh_3)_3$, $RhI(CO)(SbPh_3)_2$, $RhH(CO)(PPh_3)_3$, $Rh(AcAc)_3$, $Rh(OAc)(PPh_3)_2$, metallic Rh, $Rh_2(CO)_3$, $RhX(CO)(PPh_3)_2$, $RhCl(CO)(AsPh_3)_2$, $RhX(CO)[P(n-C_4H_9)_3]_2$, $[Rh(C_2H_4)_2Cl]_2$, $[Rh(AcO)_2]_2$, $RhCl(CO)[P(OPh)_3]_2$, $[Rh\{P(OPh)_3\}_4]_2$, $RhCl(Ph_3P)_2(CH_3I)_2$, $[Rh(CO)_2X][(n-C_4H_9)_4N]$, $[Rh_2O_2X_4]$ $[(n-C_4H_9)_4As]_2$, $[Rh(CO)I_4][(n-C_4H_9)_4P]$, $PdX_2$, $[Pd(CO)X_2]_2$, $[Pd(PPh_3)_2]_2$, $[Pd(PPh_3)]_2(CO)Br$, $[PdX_4][(n-C_4H_9)_4P]$, $Pd[(n-C_4H_9)_3P](CO)Cl_2$, $PdCl(PPh_3)_2(SnCl_3)$, $Pd[(n-C_4H_9)_3P]_2I_2$, $NiX_2$, $NiX_2 \cdot 3H_2O$, $Ni(CO)_4$, $Ni(CO)_2(PPh_3)_2$, $Ni(AcAc)_2$, metallic Ni and $Ni(OAc)_2$ (wherein X is Cl, Br or I; Ph is phenyl; OPh is phenoxy; Ac is acetyl; OAc is acetoxy; and AcAc is acetylacetonate).

The amount of these metal catalyst used is not critical, but generally, it is from $10^{-6}$ to 5 mols, preferably from $10^{-4}$ to 4 mols, more preferably from $10^{-3}$ to 2 mols, per liter of the reaction medium.

The carbonylation requires the presence of not only a metal catalyst but also a halide, and an advantageous halide is a bromide or iodide or a mixture thereof, and an iodide is preferred. The halide is generally present in the reaction medium in the form of methyl halide, acetyl halide, hydrogen halide or any mixture thereof, so it may be supplied to the reaction medium as such or a compound that forms at least one of halide, methyl halide, acetyl halide or hydrogen halide in the reaction medium may be supplied to the medium. The compound that reacts with other components in the reaction medium to form methyl halide, acetyl halide and/or hydrogen halide is inorganic halides such as alkali metal halides and alkaline earth metal halides, as well as elemental iodine and bromine.

The amount of these halides used is also not critical, but usually $10^{-6}$ to 20 mols, preferably from $10^{-4}$ to 10 mols, of halide per liter of the reaction medium interms of halogen atm is used.

As described above, the carbonylation may be performed with advantage in the presence of a catalyst system composed of a metal catalyst and halide secondary component, but it is further enhanced by using an organic or inorganic accelerator. An organic accelerator is particularly effective. The organic accelerator can be supplied to the reaction zone simultaneously with the reactants, or a metal coordination complex resulting from the separate mixing of the accelerator and catalyst metal may be supplied to the reaction zone.

Advantageous organic accelerators are organic nitrogen, phosphorus, antimony and arsenic compounds. Part of these compounds are represented by the following formula:

(wherein M is N, P, Sb or As; $R_1$, $R_2$ and $R_3$ which may be the same or different and each represents hydrogen or alkyl, cycloalkyl or aryl preferably having 10 carbon atoms or less). The following are examples of the organic reaction accelerator which are given here not for limiting purposes but for illustrative purposes only: amines such as monomethylamine, dimethylamine, trimethylamine, dimethylethylamine, diethylamine, tri-iso-propylamine, tri-n-propylamine, tri-n-butylamine, tri-tert-butylamine, aniline, dimethylaniline, and diethylaniline; phosphines such as tri-n-propylphosphine, tri-iso-propylphosphine, tri-n-butylphosphine, tri-tert-butylphosphine, tricyclo-hexylphosphine, ethylene bis(diphenylphosphine) and triphenyl-phosphine; arsines such as trimethylarsine, triethylarsine, tricyclohexylarsine, triphenylarsine, phenyl-di-iso-propylarsine, diphenylarsine, bis(diphenylarsino)ethane, and bis(di-iso-propylarsino)hexane; stibines such as tri-iso-propylstibine, ethyl-di-iso-propyl-stibine, triphenylstibine, tri(o-tolyl)-stibine, phenyldiamylstibine, tris(diethylaminomethyl)stibine and bis(diethylstibino)pentane.

Other organic nitrogen compounds which may or may not contain oxygen or phosphorus atom are used with advantage as the organic reaction accelerator. Non-limiting examples of these compounds include heterocyclic compounds such as pyrrole, pyrrolidine, piperidine, pyrimidine, picolines, pyrazine and $N-C_{1-5}$ lower alkyl substituted derivatives thereof such as N-methylpyrrolidine, benzotriazole, piperazine, N-methyl piperazine, N-ethylpiperazine, 2-methyl-N-methylpiperazine, 2,2-dipyridyl, methyl-substituted 2,2-dipyridyl, 1,4-diazabicyclo(2,2,2)octane, methyl-substituted 1,4-diazabicyclo(2,2,2)octane, purine, 2-amino-pyridine, 1,10-phenanthroline, methyl-substituted 1,10-phenanthroline, 2-(dimethylamino)-pyridine, 2-(dimethylamino)-6-methoxyquinoline, 7-chloro-1,10-phenanthroline, 4-triethylsilyl-2,2'-dipyridyl, 5-(thiabenzyl)-1,10-phenanthroline, pyridine, 2,4-dimethyl pyridine, 2,6-dimethyl pyridine, 2,4,6-trimethylpyridine, and imidazole; diamines, such as N,N,N',N'-tetramethylethylenediamine, N,N,N',N'-tetraethylethylenediamine, N,N,N',N'-tetra-n-propylethylenediamine, N,N,N',N'-tetramethylemethylenediamine, N,N,N',N'-tetraethylethylenediamine, and N,N,N',N'-tetra-iso-butylmethylenediamine; and nitrilies, such as acetonitrile, propionitrile, adiponitrile, and benzonitrile.

The organic compounds having oxygen or phosphorus atom and nitrogen atom include hydroxyl or carboxyl-substituted compounds of the above mentioned organic nitrogen compounds, such as 2-hydroxypyridine, methyl-substituted 2-hydroxypyridine, picolinic acid, methyl-substituted picolinic acid, 2,5-dicarboxypiperazine, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, salts of ethylenediaminetetraacetic acid, such as tetramethyl ester of ethylenediaminetetraacetic acid, ammonium salts like ammonium acetate; carboxylic amides, such as acetamide, acetanilide, N,N-dimethylacetamide, and N-methyl-N-phenylacetamide; amino acids, such as N,N-dimethylglycine, and N,N-diethylglycine; 1-methyl-2-pyrrolidinone, 4-methylmorpholine, N,N,N',N'-tetramethylurea, N-methyliminodiacetic aicd, nitrilotriacetic acid, and N-methyl iminodiacetic acid; and phosphine iminium salts such as triphenylphosphine iminium chloride. Organic reaction accelerators having trivalent nitrogen and phosphrus are particularly preferred.

Effective inorganic accelerators include metals having atomic weight of at least 6 and belonging to Groups Ia, IIa, IIIa, IVa, Ib, IIb, Vb, VIb and VIIb of the Periodic Table and compounds of these metals. Metals of these groups having atomic weight of less than 120 are preferred. Lithium, sodium, potassium, magnesium, calcium, aluminum, tin, zinc, cadmium, copper, manganese, chromium, and vanadium are preferred. The inorganic accelerator may be used in a finely divided elemental form, or it may be used in various inorganic or organic compounds effective for introducing an element into the reaction system in a cationic form under reaction conditions. Therefore, typical compound of element as inorganic accelerator include oxides, hydroxides, halides preferably bromide and iodide, oxyhalides, hydrides, carbonyls, alkoxides, nitrates, nitrides, phosphates, and aliphatic, alicyclic, naphthenic and aryl-aliphatic monocarboxylates such as acetate, butyrate, decanoate, laurate, stearate and benzoate. Other advantageous compounds are metal alkyls, chelates, associate compounds and enol salts. Particularly advantageous inorganic accelerators are bromides, iodides and organic acid salts preferably acetates. If desired, the catalytic metal may be combined to advantage with organic and inorganic accelerators. The amount of the organic or inorganic accelerator depends on the amount of the catalytic metal in the reaction zone, and generally $10^{-6}$ to 10 mols, preferably from $10^{-4}$ to 5 mols, per liter of the reaction medium is used.

The carbonylation for performing the process of this invention may be suitably carried out at a temperature between 40° and 450° C., preferably between 80° C. and 300° C., more preferably between 100° and 250° C. Carbon monoxide preferably has a partial pressure between 0.5 and 350 atm., more preferably between 1 and 300 atm., and most preferably between 3 and 250 atm. A partial pressure may be in the range of from 0.05 to 100 atm. Carbon monoxide need not always have high purity and it may contain hydrogen, carbon dioxide, methane, nitrogen, or rare gas. Carbon monoxide of extremely low purity is not preferred because it increases the pressure of the reaction system. The effluent from the carbonylation zone is freed of acetic anhydride by a suitable separation technique such as distillation, and the unreacted methyl acetate, iodine and metal catalytic component are recovered and recycled to the carbonylation zone. The separation zone usually consists of more than one distillation unit, such as flash distillation column and/or separation column. The distillation unit is typically used at a temperature between 40° and 200° C. and a pressure less than 5 atm. Part or all of the unreacted waste gas from the step (b) can be used as supply gases for the step (a). Such recycling of supply gases and unreacted waste gas constitute an effective embodiment.

Step (c):

In the step (c), ED (ethylidene diacetate) and methyl acetate are formed in the ED synthesis zone through the reaction between acetaldehyde and/or dimethylacetal and acetic anhydride. The conversion to ED does not necessarily require a catalyst, but it is performed with advantage in the presence of an acid catalyst (as described in U.S. Pat. No. 2,021,698 and Japanese Patent Application No. 117659/79 filed by the present applicant).

The following are examples of the acid catalyst for use in this invention which are given here not for limiting purposes but for illustrative purposes only: Bronsted acids such as HI, HBr, HCl, HF, $H_2SO_4$, $HNO_3$, $H_3PO_4$, $H_3BO_3$, $HClO_3$, $HBrO_3$, $HIO_3$, polyphosphoric acid, benzenesulfonic acid, and alkylbenzenesulfonic acid; Lewis acids of halides having a central atom of Groups IIa, IIIa, IVa, Va, VIa, IIIb, IVb, Vb, VIb, VIIb and VIII of the periodic table, such as $PbX_2$, $MgX_2$, $BX_3$, $B_2X_4$, $AlX_3$, $GaX_2$, $GaX_3$, $InX$, $InX_2$, $InX_3$, $TlX$, $TlX_3$, $TlX_4$, $SiX_4$, $Si_2X_6$, $Si_3X_8$, $Si_4X_{10}$, $Si_5X_{12}$, $GeX$, $GeX_2$, $GeX_4$, $SnX_2$, $SnX_4$, $PX_3$, $PX_5$, $P_2X_4$, $AsX_3$, $AsX_5$, $SbX_3$, $SbX_5$, $BiX$, $BiX_2$, $BiX_3$, $TiX_2$, $TiX_3$, $TiX_4$, $ZrX_2$, $ZrX_3$, $ZrX_4$, $VX_2$, $VX_3$, $VX_4$, $CrX_2$, $CrX_3$, $MoX_2$, $MoX_3$, $MoX_4$, $MoX_5$, $WX_2$, $WX_4$, $WX_5$, $WX_6$, $MnX_2$, $MnX_3$, $MnX_4$, $ReX_3$, $ReX_4$, $ReX_6$, $FeX_2$, $FeX_3$, $CoX_2$, $CoX_3$, $CoX_4$, $NiX_2$, $RuX$, $RuX_2$, $RuX_3$, $RuX_4$, $CuX$, $CuX_2$, $AuX$, $AuX_2$, $AuX_3$, $ZnX_2$, $CdX_2$, $Hg_2X_2$, $HgX_2$ (wherein X is F, Cl, Br or I). Particularly preferred are $MgCl_2$, $MgBr_2$, $MgI_2$, $BF_3$, $BCl_3$, $BI_3$, $AlCl_3$, $AlBr_3$, $AlI_3$, $SiCl_4$, $GeCl_4$, $SnCl_4$, $SnBr_4$, $SnI_4$, $SbCl_5$, $SbBr_3$, $SbCl_3$, $TiCl_4$, $TiBr_4$, $TiI_4$, $CrCl_3$, $CrBr_3$, $MoCl_5$, $WCl_6$, $FeCl_3$, $FeBr_3$, $FeI_3$, $CoCl_2$, $CoBr_2$, $NiCl_2$, $NiBr_2$, $NiI_2$, $CuCl$, $CrBr$, $CuCl_2$, $CuI$, $ZnCl_2$, $ZnBr_2$ and $ZnI_2$ Lewis acids such as $B(CH_3)_3$ and $SO_3$ are also used with advantage as the catalyst.

Besides these homogeneous catalysts, solid acids can also be used to facilitate the separation from the reaction products and prevent the corrosion of the reactor. Examples of the effective solid catalyst include clays such as kaolinite, bentonite, attapulgite, montmorillonite, clarite, Fuller's earth and zeolites; solidified acids wherein $H_2SO_4$, $H_3PO_4$ and $H_3BO_3$ are attached to silica, quartz sand, alumina and diatomaceous earth; cation exchange resins; charcoal heattreated at a temperature near 300° C.; solid inorganic compounds such as ZnO, $Al_2O_3$, $ThO_2$, $TiO_2$, $ZrO_2$, $CeO_2$, $As_2O_3$, $V_2O_3$, $Bi_2O_3$, $SiO_2$, $Cr_2O_3$, $MoO_2$, ZnS, CaS, $CaSO_4$, $MnSO_4$, $NiSO_4$, $CuSO_4$, $CoSO_4$, $CdSO_4$, $SrSO_4$, $ZnSO_4$, $MgSO_4$, $FeSO_4$, $BaSO_4$, $KHSO_4$, $K_2SO_4$, $Al_2(SO_4)_3$, $Fe_2(SO_4)_3$, $Cr_2(SO_4)_3$, $Ca(NO_3)_2$, $Ni(NO_3)_2$, $Fe(NO_3)_3$, $BPO_4$, $FePO_4$, $CrPO_4$, $Ti_3(PO_4)_4$, $Zr_3(PO_4)_4$, $Cu_3(PO_4)_2$, $Ni_3(PO_4)_2$, $AlPO_4$, $Zn_3(PO_4)_2$, $Mg(PO_4)_2$; solid composite acid compounds such as $SiO_2$—$Al_2O_3$, $B_2O_3$—$Al_2O_3$, $Cr_2O_3$—$Al_2O_3$, $MoO_2$—$Al_2O_3$, $MoO_3$—$SiO_2$, $ArO_2$—$SiO_2$, $Ga_2O_3$—$SiO_2$, BeO—$SiO_2$, MgO—$SiO_2$, CaO—$SiO_2$, SrO—$SiO_2$, $Y_2O_3$—$SiO_2$, $La_2O_3$—$SiO_2$, SnO—$SiO_2$, PbO—$SiO_2$, $MoO_3$—$Fe_2(MoO_4)_3$, $TiO_2$—ZnO, $TiO_2$—$ZrO_2$, $TiO_2$—$SiO_2$, $TiO_2$—$SnO_2$, $TiO_2$—$WO_3$, $TiO_2$—$MoO_3$, $TiO_2$—$Sb_2O_3$, $TiO_2$—$Fe_2O_3$, $TiO_2$—$Cr_2O_3$, $TiO_2$—$V_2O_3$, $TiO_2$—$Mn_2O_3$, $TiO_2$—$Co_3O_4$, $TiO_2$—NiO, $TiO_2$—CuO, $TiO_2$—$Al_2O_3$, $TiO_2$—$Bi_2O_3$, $TiO_2$—CdO, ZnO—$Bi_2O_3$, ZnO—$As_2O_3$, ZnO—$Al_2O_3$, ZnO—$SiO_2$, ZnO—$ZrO_2$, ZnO—$Fe_2O_3$, $ZrO_2$—$ThO_2$, $Al_2O_3$—NiO, $Al_2O_3$—NiO, $Al_2O_3$—$Co_3O_4$, $Al_2O_3$—CdO, $Al_2O_3$—$Fe_2O_3$, $Al_2O_3$—$Bi_2O_3$, $Al_2O_3$—$ZrO_2$, $ZrO_2$—CdO, $TiO_2$—MgO.

The homogeneous catalysts of Lewis acid type are used with particular advantage at low temperatures.

The homogeneous acid catalyst is used in this invention generally in an amount less than 2 mols, preferably between $10^{-6}$ to 1.5 mols per mol of the reaction medium. A particularly preferred range is from $10^{-4}$ to 1.0 mol. If desired, a high catalyst level of about 2 mols may be used. The amount of the solid catalyst used is suitably determined by the type. and activity of the catalyst used, and for use in a fluidized bed, the catalyst is used in solution generally in an amount of from about 0.01 to 25 wt %, preferably from about 0.1 to 10 wt %. For use on a fixed bed, a reactor packed with the solid acid and held at a predetermined temperature is supplied with a reaction medium containing acetaldehyde and/or dimethylacetal and acetic anhydride for catalytic reaction.

If the same catalyst is to be used in both steps (c) and (d), aromatic or aryl sulfonic acids such as benzenedulfonic acid, toluenesulfonic acid, xylenesulfonic acid and naphthalenesulfonic acid are optimum as such catalyst.

The reaction for the step (c) can be peformed at a temperature which is selected from a wide range depending upon the type and activity of the catalyst. Usually, a temperature in the range of from $-10°$ to $350°$ C., preferably from $-5°$ to $300°$ C., more preferably from $0°$ to $250°$ C. is used.

Detailed mechanism of the reaction for the step (c) is not clearly defined, but the formation of ED and methyl acetate can be schematically represented by the following chemical formulae:

$$CH_3CHO + (CH_3CO)_2O \rightarrow CH_3CH(OCOCH_3)_2$$

$$CH_3CH(OCH_3)_2 + 2(CH_3CO)_2O \rightarrow CH_3CH(OCOCH_3)_2 + 2CH_3COOCH_3$$

The above formulae for the formation of ED indicate that the stoichiometric amount of acetic anhydride can vary with the proportion of acetaldehyde to dimethylacetal. For higher conversion of acetaldehyde and dimethylacetal to ED and higher thermal decomposition of ED to vinyl acetate and acetic acid in the next step (d), acetic anhydride is preferably used in large excess of the stoichiometric amount; from 2.5 to 100 mols, preferably from 5 to 60 mols, of acetic anhydride per mol of acetaldehyde and dimethyl-acetal is used. The large excess of acetic anhydride is readily supplied by recycling a stream of acetic anhydride between the step (c) and step (d). The effluent from the step (c) is usually directed to the subsequent step (d), but if desired, a low-boiling product methyl acetate may be separated from the effluent by a separator incorporated in the step (c) for recycle to the carbonylation step (b). The separator consists of more than one distillation unit that is composed of, say, flash distillation column or separation column, and it is typically operated at a temperature between $30°$ and $200°$ C. and a pressure less than 5 atm. Acetic anhydride as a material for the step (c) is generally supplied from the step (b) by carbonylation of methyl acetate, but depending on the need, part of the acetic anhydride may be produced by the Wacker process wherein acetic anhydride is derived from ketene.

Step (d):

In this step, the ED-containing effluent from the step (c) is thermally decomposed. The reaction taking place in this thermal decomposition zone is schematically represented as follows:

$$CH_3CH(OCOCH_3)_2 \rightarrow CH_2=CHOCOCH_3 + CH_3COOH$$

The conversion reaction in the decomposition zone is typically performed at a temperature between $50°$ and $200°$ C. and a pressure less than 15 atm. The effluent vapor from the thermal decomposition zone is a mixture of vinyl acetate, acetic acid, unreacted acetaldehyde and acetic anhydride, unconverted ED or methyl acetate. The mixture is fed to a separation zone where it is separated into the respective necessary components. The separation zone consists of more than one distillation unit such as flash distillation column and/or separation column. The separation zone is typically operated at a temperature between $25°$ and $200°$ C. and a pressure less than 5 atm.

The vapor effluent coming from the step (d) is separated under the above operating conditions into a stream of product vinyl acetate, a stream of acetic acid, a recycling stream of acetaldehyde, a recycling/supply stream of methyl acetate and a high-boiling recycling stream to be recycled to the ED synthesis zone. In the decomposition zone, the decomposition of ED may be accompanied by the formation of a polymerization by-product, and so, to prevent the accumulation of the by-product in the reaction system, part of the decomposition residue may be discharged from the reaction system depending upon the need. The acetic acid recovered from the step (d) is usually used as a product, but if necessary, it may be esterified with methanol by a known method and the resulting methyl acetate is supplied to the step (b) for carbonylation. As described before, vinyl acetate that is also formed as a product is converted to PVA and methyl acetate through reaction with vinyl acetate polymer and methanol.

Step (e):

Methyl acetate produced in the steps (a) and (c) by a method well known in the art is recycled to the carbonylation step (b). The steps (c), (d) and (e) may be integrated into one step to provide a simple process, and this is preferred in industrial operation of the process of this invention so long as the overall balance of the reactions is not upset by such integration.

As described in the foregoing, this invention produces ethanol, vinyl acetate and acetic acid from $C_1$ compounds such as $CH_4$, $CO-H_2$ and $CH_3OH$ rather than from olefins such as ethylene that are currently used as starting materials or intermediates in the petrochemical industry. As a further advantage, since hydrocarbonylation is integrated in a complex process, most of the gases supplied need no separation step such as low-temperature processing. Methanol, acetaldehyde, methyl acetate and dimethylacetal supplied or recycled to the process, particularly the steps (a), (b) and (c), need not be individually purified to high purity and they permit each other as impurities, so an overall balance of the process can be easily obtained.

In short, the complex process of this invention that has five steps integrated therein achieves several advantages over the existing process for producing ethanol, vinyl acetate and acetic acid from ethylene.

Figure 1:
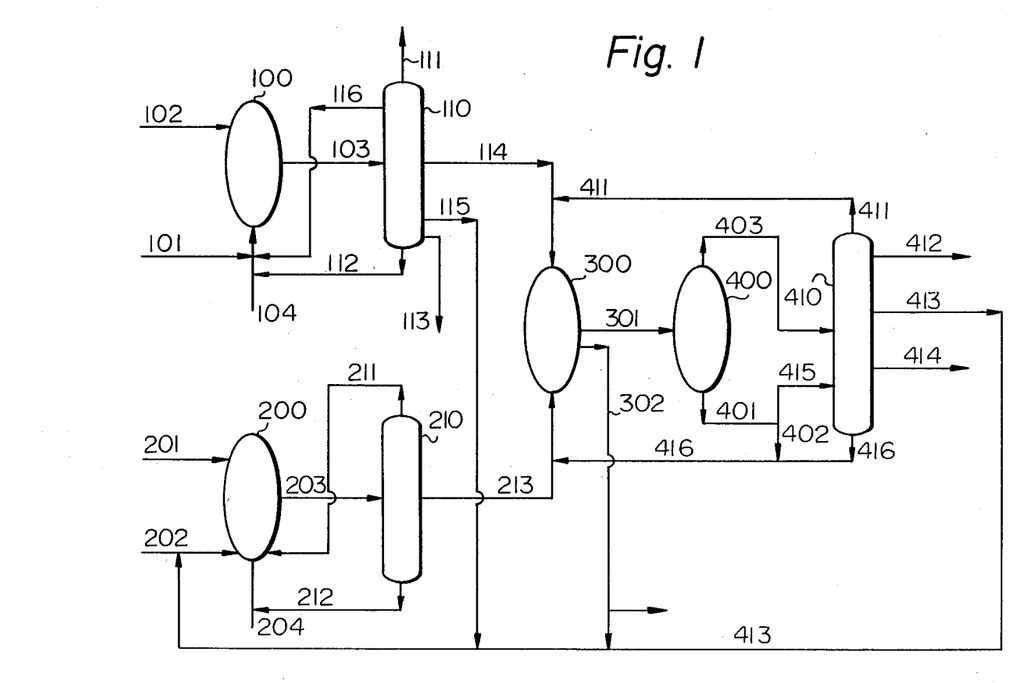
FIG. 1 is a flow sheet illustrating an embodiment of the process of this invention.

For better understanding of this invention, one preferred embodiment of the invention is described hereunder by reference to the accompanying drawing. In the drawing, a hydrocarbonylation zone (100) is composed of more than one pressure vessel of any type and contains a suitable catalyst system typically consisting of a cobalt metal catalyst and a halide secondary component. The vessel is supplied under pressure with a recycling working fluid as well as methanol, carbon monoxide and hydrogen. Carbon monoxide and hydrogen are supplied by a line (102) and methanol by a line (101). The catalyst and high-boiling component in the reaction mixture are recycled through a line (112) as will be described hereunder, and if necessary, an additional catalyst component is provided through a line (104). Hydrocarbonylation is performed by a batchwise process, semi-continuous process or continuous process, and continuous flow reaction is preferred in industrial operation. This is true with the subsequent steps to be described hereunder. The reaction mixture flowing from the hydrocarbonylation zone (110) is directed to a separation zone (11) via a line (103) and separated into the necessary components. Ethanol, one of the end products, and the resulting water containing acetic acid are recovered from the system via a line (111) and (113), respectively, for use as materials for the synthesis of methyl acetate or for purification to a product quality. Unreacted methanol is withdrawn via a line (116) and recycled to the hydrocarbonylation zone (100). The high-boiling component in the reaction mixture that contains the catalytic component is recycled to the hydrocarbonylation zone (100) via a line (112). The by-product methyl acetate is supplied to a carbonylation zone (200) via a line (115) for use as a material for the synthesis of acetic anhydride. An effluent containing dimethylacetal and acetaldehyde as the other end products is supplied to an ED synthesis zone (300) through a line (114).

The carbonylation zone (200) composed of more than one pressure reactor of a desired type is supplied with methyl acetate as the material for the synthesis of acetic anhydride. Methyl acetate is usually supplied as a recycle through lines (115) and (413) or (302), but if desired, additional methyl acetate may be supplied through a line (202). Preferably, methyl acetate produced from acetic acid formed in the step (a), (c) or (d) methanol or methyl acetate formed as a by-product in the production of PVA is used as part of the starting material. Carbon monoxide is supplied through a line (201) under pressure, and the catalyst and heavy components in the reaction mixture are recycled through a line (212). If necessary, an additional catalyst component is supplied through a line (204). The reaction mixture flowing out of the carbonylation zone (200) is directed to a separation zone (210) where it is separated into the necessary components. Methyl iodide and methyl acetate, i.e. low-boiling components in the reaction mixture, are recycled to the carbonylation zone (200) mainly through a line (211). The acetic anhydride produced is supplied to the ED synthesis zone (300) through a line (213). As will be described hereunder, a stream of acetic anhydride originating from a thermal decomposition zone (400) and a separation zone (410) through a line (416) combines with the stream of acetic anhydride being additionally supplied to the ED synthesis zone (300) and the combined stream the volume of which has been apprently increased is supplied to the synthesis zone (300).

In the ED synthesis zone (300), the stream of acetaldehyde containing dimethylacetal is reacted with acetic anhydride in the presence of an acid catalyst, and at least part of the reactants is converted to ED and methyl acetate. The reaction mixture is usually fed to the thermal decomposition zone (400) through a line (301), but if desired, methyl acetate in the mixture may be separated by a method well known in the art, and is recycled to the carbonylation zone (200) through a line (302).

In the thermal decomposition zone (400), ED is converted to vinyl acetate and acetic acid by thermal decomposition. The vapor stream from the thermal decomposition zone (400) is primarily a mixture of vinyl acetate, acetaldehyde, acetic anhydride, acetic acid, methyl acetate and undecomposed ED, and it enters the separation zone (410) through a line (403) and separated into the desired components there. The catalyst-containing liquid in the decomposition zone (400) is recycled to the ED synthesis zone (300), so it is withdrawn from a line (402) through a line (401). The line (402) communicates with a line (416). Alternatively, part or all of the liquid is fed to the separation zone (410) through a line (415). The separation zone (410) is composed of more than one distillation unit, and low-boiling acetaldehyde and methyl acetate are separated from vinyl acetate in that zone. Acetaldehyde is returned to the ED synthesis zone (300) through a line (411), and methyl acetate is recycled to the carbonylation zone (200) through a line (413). The product vinyl acetate is withdrawn through a line (412) and purified to give a product quality. A polymerization inhibitor such as hydroquinone may be added with advantage to the vinyl acetate for providing longer shelf life. Acetic acid is also withdrawn through a line (414) and purified to give a product quality. If necessary, acetic acid may be esterified with methanol to synthesize methyl acetate that can be recycled to the carbonylation zone (200).

For better understanding of the foregoing description, a summary of the concept of the steps (a) to (d) is given below by schematic representation:

Step (a)

(i) $CH_3OH + CO + H_2 \rightarrow CH_3CHO + H_2O$ (ii) $2CH_3OH + CO \rightarrow CH_3COOCH_3 + H_2O$

(iii) $3CH_3OH + CO + H_2 \rightarrow CH_3CH(OCH_3)_2 + 2H_2O$

Step (b)

(iv) $3CH_3COOMe + 3CO \rightarrow 3(CH_3CO)_2O$

Step (c)

(v) $CH_3CHO + (CH_3CO)_2O \rightarrow CH_3CH(OCOCH_3)_2$ (vi) $CH_3CH(OCH_3)_2 + 2(CH_3CO)_2O \rightarrow CH_3CH(OCOCH_3)_2 + 2CH_3COOCH_3$ Step (d)

(vii) $2CH_3CH(OCOCH_3)_2 \rightarrow 2CH_2=CHOCOCH_3 + 2CH_3COOH$

These formulae indicate that the combination of the steps (a) through (d) integrated in the complex process of this invention enables the production of vinyl acetate from material consisting of methanol, carbon monoxide and hydrogen.

This invention is now described in greater detail by reference to the non-limiting following examples. Unless otherwise specified all parts in the examples are by mole.

EXAMPLE 1

Example 1 as well as the other examples were implemented according to the flow sheet outlined in FIG. 1.

A hydrocarbonylation zone (100) that included a pressure reactor was charged with feedstock and working fluid (a solution comprising 5 mmol of cobalt acetate and 1.25 mmol of iodine in one mol of methanol) which was elevated to 200° C. while the pressure within the zone was held at 50 to 400 Kg/cm²G with a gas mixture (CO:H₂=1:1). Thereafter, a liquid feedstock was supplied continuously to the bottom of the reactor through a line (101), and a gas mixture was supplied to the reactor through a line (102). A gas-liquid mixture overflowing from the top of the reactor was directed to a high-pressure separator where the separated liquid mixture was distilled to provide a stream of the resulting acetaldehyde, a stream of ethanol, a stream of methyl acetate, a stream of acetic acid and a stream of unreacted methanol. A recycling stream containing unreacted methanol, iodine supplied initially, iodides formed by reaction between iodine and other components and cobalt-containing compound was returned continuously to the reactor.

The reaction in the hydrocarbonylation zone was conducted so that the average residence time of the reactor liquor was about one hour. In the reaction, a recycling stream containing 5 parts/hr of cobalt and 1.25 parts/hr of iodine as well as about 1000 parts/hr of methanol containing about 222 parts of recycled methanol were supplied continuously under pressure. The reaction mixture was withdrawn at a rate of about 680 parts/hr and directed to a separation zone (110). In the separation zone (110), the effluent was fractionated at a pressure lower than 3 atm. and a temperature between 40° to 150° C. The recycling stream containing the catalyst components was returned to the hydrocarbonylation zone through a line (112) together with part of the stream of unreacted methanol flowing through lines (116) and (112) at a rate of 222 parts/hr. Methyl acetate was supplied to the subsequent carbonylation zone through a line (115) at a rate of 150 parts/hr, ethanol was distilled off through a line (111) at a rate of 32 parts/hr, and crude acetic acid containing the resulting water was withdrawn through a line (113) at a rate of 6 parts/hr. Crude acetaldehyde containing 85 parts of dimethylacetal and 28 parts of methanol was supplied to an ED synthesis zone (300) at a rate of 270 parts/hr through a line (114) together with a stream of acetaldehyde recycled through a line (411).

A carbonylation zone (200) including a pressure reactor equipped with a stirrer was charged with a feedstock and working fluid consisting of 1000 ppm of rhodium acetate, 0.27 mol % of triphenylphosphine, 27.8 mol % of methyl acetate, 64.6 mol % of acetic acid and 7.30 mol % of methyl iodide, and the fluid was elevated to 175° C. while the pressure within the reactor was held at 80 Kg/cm$^2$G with carbon monoxide. A liquid feedstock was supplied continuously to the reactor, and the liquid reaction mixture was withdrawn and distilled. The resulting acetic anhydride was distilled off. A recycling stream containing acetic acid (used as a solvent) and unreacted methyl acetate, methyl iodide supplied initially, iodine-containing compounds formed by reaction between methyl iodide and other components, and rhodium was returned continuously to the reactor. The reaction in the carbonylation zone was conducted so that the average residence time of the reactor liquor was about 1.5 hours. In the reaction, a recycling stream containing 156 parts/hr of methyl iodide, $1.42 \times 10^{-2}$ parts/hr of rhodium and 5.74 parts/hr of triphenylphosphine, as well as about 589 parts/hr of methyl acetate containing 234 parts of recycled methyl acetate were supplied continuously to the carbonylation zone (200) under pressure. As will be described hereunder, the stream of methyl acetate supplied consisted of a stream supplied at a rate of 348 parts/hr through lines (115) and (302) and methyl acetate additionally supplied at a rate of 7 parts/hr. The reaction mixture was withdrawn at a rate of 2110 parts/hr and directed to a separation zone (210). In the separation zone (210), the reaction mixture was flash-distilled at a pressure less than 3 atm. and a temperature between 140° and 160° C., and the catalytic components and heavy components from the flash distillation containing part of methyl acetate, part of acetic acid and part of acetic anhydride were recycled to the carbonylation zone (200) at a rate of about 680 parts/hr.

Vapor obtained by flash distillation was fractionated at a pressure lower than 3 atm. and a temperature between 40° and 160° C. A light component comprising methyl acetate and methyl iodide was distilled off at a rate of about 390 parts/hr and recycled to the carbonylation zone through a line (211), and a medium component consisting of acetic acid was recycled to the carbonylation zone (200) through lines (211) and (212) at a rate of 685 parts/hr. A high-boiling component or acetic anhydride that was obtained by fractional distillation was fed to an ED synthesis zone (300) at a rate of about 355 parts/hr through a line (213). The zone (300) was composed of a reactor equipped with a stirrer and was operated at 70° C.

The crude acetaldehyde stream comprising dimethylacetal, methanol and acetaldehyde was supplied to the ED synthesis zone through a line (114) at a rate of 270 parts/hr together with a recycling stream supplied through the line (411) that consisted of 41 parts/hr of recycled acetaldehyde, about 125 parts/hr of ED and about 2375 parts/hr of acetic anhydride. In order to maintain the content of benzenesulfonic acid in the working fluid at about 3.3 wt %, fresh benzenesulfonic acid was added to the working fluid recycled from the ED synthesis zone (300) to the decomposition zone (400), if necessary. The effluent from the ED synthesis zone was optionally separated in that zone into a stream of methyl acetate supplied through a line (302) to the carbonylation zone at a rate of 198 parts/hr, a stream of acetic acid that was discharged from the reaction system at a rate of 28 parts/hr, and a stream of ED and acetic anhydride supplied to the decomposition zone (400) through a line (301). To be more specific, ED and acetic anhydride were supplied to the decomposition zone (400) through the line (301) at rates of about 408 parts/hr and about 2334 parts/hr, respectively. The decomposition zone was composed of a reactor held at 135° C. and equipped with a stirrer. A mixture from the decomposition zone through lines (403) and (415) that consisted of acetaldehyde (ca. 41 parts/hr), vinyl acetate (ca. 242 parts/hr), acetic acid (ca. 242 parts/hr), acetic anhydride (ca. 2375 parts/hr) and ED (ca. 125 parts/hr) was supplied to a separation zone (410). In the separation zone, acetaldehyde was obtained as a light component at about 2.6 atm. and at 45° C., and was recycled to the ED synthesis zone (300) through the line (411). Vinyl acetate and acetic acid were separated at 1–2 atm. and at 45°–155° C.; acetic acid was distilled off through a line (414) at a rate of about 242 parts/hr and vinyl acetate distilled off through a line (412) at a rate of about 242 parts/hr.

EXAMPLE 2

A hydrocarbonylation zone (100) that included a pressure reactor was charged with a feedstock and working fluid (a solution comprising 1.3 mmol of cobalt acetate and 1.3 mmol of iodine in one mol of methanol) which was elevated to 85°–190° C. while the pressure within the zone was held at 300 to 400 Kg/cm$^2$G with a gas mixture (CO:H$_2$=1:1.4). Thereafter, a liquid feedstock was supplied continuously to the bottom of the reactor through a line (101), and a gas mixture was supplied to the reactor through a line (102). A gas-liquid mixture overflowing from the top of the reactor was directed to a high-pressure separator where the separated liquid mixture was distilled to provide a stream of the resulting acetaldehyde, a stream of ethanol, a stream of methyl acetate, a stream of acetic acid and a stream of unreacted methanol. A recycling stream containing unreacted methanol, iodine supplied initially, iodides formed by reaction between iodine and other components and cobalt-containing compound was returned continuously to the reactor.

The reaction in the hydrocarbonylation zone was conducted so that the average residence time of the reactor liquor was about 1.5 hours. In the reaction, a recycling stream containing 1.3 parts/hr of cobalt and 1.3 parts/hr of iodine as well as about 1000 parts/hr of methanol containing about 171 parts of recycled methanol were supplied continuously under pressure. The reaction mixture was withdrawn at a rate of about 722 parts/hr and directed to a separation zone (110). In the separation zone (110), the effluent was fractionated at a pressure lower than 3 atm. and a temperature between 40° and 150° C. The recycling stream containing the catalyst components was returned to the hydrocarbonylation zone through a line (112) together with part of the stream of unreacted methanol flowing through lines (116) and (112) at a rate of 171 parts/hr. Methyl acetate was supplied to the subsequent carbonylation zone through a line (115) at a rate of 170 parts/hr, ethanol was distilled off through a line (111) at a rate of 90 parts/hr, and crude acetic acid containing the resulting water was withdrawn through a line (113) at a rate of 29 parts/hr. Crude acetaldehyde containing 54 parts of dimethylacetal and 18 parts of methanol was supplied to an ED synthesis zone (300) at a rate of 262 parts/hr through a line (114) together with a stream of acetaldehyde recycled through a line (411).

A carbonylation zone (200) including a pressure reactor equipped with a stirrer was charged with a feedstock and working fluid consisting of 0.39 wt % of nickel, 1.34 mol % of triphenylphosphine, 42.4 mol % of methyl acetate, 42.4 mol % of acetic acid and 13.3 mol % of methyl iodide, and the fluid was elevated to 200° C while the pressure within the reactor was held at 58 Kg/cm$^2$G with carbon monoxide. A liquid feedstock was supplied continuously to the reactor, and the liquid reaction mixture was withdrawn and distilled. The resulting acetic anhydride was distilled off. A recycling stream containing acetic acid (used as solvents) and unreacted methyl acetate, methyl iodide supplied initially, iodine-containing compounds formed by reaction between methyl iodide and other components, and nickel was returned continuously to the reactor. The reaction in the carbonylation zone was conducted so that the average residence time of the reactor liquor was about 2.5 hours. In the reaction, a recycling stream containing 198 parts/hr of methyl iodide, 7.9 parts/hr of nickel and 20.0 parts/hr of triphenylphosphine, as well as about 632 parts/hr of methyl acetate containing 316 parts of recycled methyl acetate were supplied continuously to the carbonylation zone (200) under pressure. As will be described hereunder, the stream of methyl acetate supplied consisted of a stream supplied at a rate of 296 parts/hr through lines (115) and (413) and methyl acetate additionally supplied at a rate of 20 parts/hr. The reaction mixture was withdrawn at a rate of 1462 parts/hr and directed to a separation zone (210). In the separation zone (210), the reaction mixture was flash-distilled at a pressure less than 3 atm. and a temperature between 140° and 160° C., and the catalytic components and heavy components from the flash distillation containing part of methyl acetate, part of acetic acid and part of acetic anhydride were recycled to the carbonylation zone (200) at a rate of about 332 parts/hr. Vapor obtained by flash distillation was fractionated at a pressure lower than 3 atm. and a temperature between 40° and 160° C. A light component comprising methyl acetate and methyl iodide was distilled off at a rate of about 514 parts/hr and recycled to the carbonylation zone through a line (211), and a medium component consisting of acetic acid was recycled to the carbonylation zone (200) through lines (211) and (212) at a rate of 300 parts/hr. A high-boiling component or acetic anhydride that was obtained by fractional distillation was fed to an ED synthesis zone (300) at a rate of about 316 parts/hr through a line (213). The zone (300) was composed of a reactor equipped with a stirrer and was operated at 70° C.

The crude acetaldehyde stream comprising dimethylacetal, methanol and acetaldehyde was supplied to the Ed synthesis zone through a line (114) at a rate of 262 parts/hr together with a recycling stream supplied through the line (411) that consisted of 41 parts/hr of recycled acetaldehyde, about 126 parts/hr of Ed and about 2394 parts/hr of acetic anhydride. In order to maintain the content of benzenesulfonic acid in the working fluid at about 3.3 wt %, fresh benzenesulfonic acid was added to the working fluid recycled from the ED synthesis zone (300) to the decomposition zone (400), if necessary. The effluent from the ED synthesis zone that was a mixture of methyl acetate (ca. 126 parts/hr), acetic acid (ca. 18 parts/hr), Ed (ca. 411 parts/hr) and acetic anhydride (ca. 2353 parts/hr) was supplied to the decomposition zone (400) through the line (301). The decomposition zone was composed of a reactor held at 135° C. and equipped with a stirrer. A mixture from the decomposition zone through lines (403) and (415) that consisted of acetaldehyde (ca. 41 parts/hr), vinyl acetate (ca. 244 parts/hr), acetic acid (ca. 262 parts/hr), acetic anhydride (ca. 2394 parts/hr) and Ed (ca. 126 parts/hr) was supplied to a separation zone (410). In the separation zone, acetaldehyde was obtained as a light component at about 2.6 atm. and at 45° C., and was recycled to the ED synthesis zone (300) through the line (411). Vinyl acetate, acetic acid and methyl acetate were separated at 1-3 atm. and at 40°-160° C.; acetic acid was distilled off through a line (414) at a rate of about 262 parts/hr and vinyl acetate distilled off through a line (412) at a rate of about 244 parts/hr. Methyl acetate was supplied to the carbonylation zone (200) through a line (413) at a rate of 126 parts/hr.

These formula indicate that the combination of the steps (a) through (d) integrated in the complex process of this invention enables the production of vinyl acetate from material consisting of methanol, carbon monoxide and hydrogen.

EXAMPLE 3

A hydrocarbonylation zone (100) that included a pressure reactor was charged with a feedstock and working fluid (a solution comprising 1.5 mmol of cobalt acetate, 1.25 mmol of iodine and 0.1 mol of methyl acetate in one mol of methanol) which was elevated to 195° C. while the pressure within the zone was held at 400 Kg/cm$^2$G with a gas mixture CO:H$_2$=1:1.1). Thereafter, a liquid feedstock was supplied continuously to the bottom of the reactor through a line (101), and a gas mixture was supplied to the reactor through a line (102). A gas liquid mixture overflowing from the top of the reactor was directed to a high-pressure separator where the separated liquid mixture was distilled to provide a stream of the resulting acetaldehyde, a stream of ethanol, a stream of methyl acetate, a stream of acetic acid and a stream of unreacted methanol. A recycling stream containing unreacted methanol, iodine supplied initially, iodides formed by reaction between iodine and other components and cobalt-containing compound was returned continuously to the reactor.

The reaction in the hydrocarbonylation zone was conducted so that the average residence time of the reactor liquor was about 0.8 hours. In the reaction, a recycling stream containing 1.5 parts/hr of cobalt and 1.25 parts/hr of iodine as well as about 1000 parts/hr of methanol containing about 403 parts of recycled methanol and 100 parts/hr of recycled methyl acetate were supplied continuously under pressure. The reaction mixture was withdrawn at a rate of about 957 parts/hr and directed to a separation zone (110). In the separation zone (110), the effluent was fractionated at a pressure lower than 3 atm. and a temperature between 40° and 150° C. The recycling stream containing the catalyst components was returned to the hydrocarbonylation zone through a line (112) together with part of the stream of unreacted methanol (403 parts/hr) and recycled methyl acetate (100 parts/hr) flowing through lines (116) and (112). Methyl acetate was supplied to the subsequent carbonylation zone through a line (115) at a rate of 95 parts/hr, ethanol was distilled off through a line (111) at a rate of 12 parts/hr, and crude acetic acid containing the resulting water was withdrawn through a line (113) at a rate of 7 parts/hr. Crude acetaldehyde containing 24 parts of dimethylacetal and 8 parts of methanol was supplied to an ED synthesis zone (300) at a rate of 340 parts/hr through a line (114) together with a stream of acetaldehyde recycled through a line (411).

A carbonylation zone (200) including a pressure reactor equipped with a stirrer was charged with a feedstock and working fluid consisting of 0.45 wt % of nickel, 1.33 mol % of triphenylphosphine, 42.4 mol % of methyl acetate, 42.4 mol % of acetic acid and 13.2 mol % of methyl iodide, and the fluid was elevated to 200° C. while the pressure within the reactor was held at 58 Kg/cm$^2$ G with carbon monoxide. A liquid feedstock was supplied continously to the reactor, and the liquid reaction mixture was withdrawn and distilled. The resulting acetic anhydride was distilled off. A recycling stream containing acetic acid (used as solvents) and unreacted methyl acetate, methyl iodide supplied initially, iodine-containing compounds formed by reaction between methyl iodide and other components, and nickel was returned continuously to the reactor. The reaction in the carbonylation zone was conducted so that the average residence time of the reactor liquor was about 2.5 hours. In the reaction, a recycling stream containing 227 parts/hr of methyl iodide, 11.9 parts/hr of nickel and 22.9 parts/hr of triphenylphosphine, as well as about 728 parts/hr of methyl acetate containing 364 parts of recycled methyl acetate were supplied continuously to the carbonylation zone (200) under pressure. As will be described hereunder, the stream of methyl acetate supplied consisted of a stream supplied at a rate of 151 parts/hr through lines (115) and (302) and methyl acetate additionally supplied at a rate of 7 parts/hr by esterification of acetic acid derived from a decomposition zone (400) and a separation zone (410). The reaction mixture was withdrawn at a rate of 1683 parts/hr and directed to a separation zone (210). In the separation zone (210), the reaction mixture was flash-distilled at a pressure less than 3 atm. and a temperature between 140° and 160° C., and the catalytic components and heavy components from the flash distillation containing part of methyl acetate, part of acetic acid and part of acetic anhydride were recycled to the carbonylation zone (200) at a rate of about 428 parts/hr. Vapor obtained by flash distillation was fractionated at a pressure lower than 3 atm. and a temperature between 40°and 160° C. A light component comprising methyl acetate and methyl iodide was distilled off at a rate of about 591 parts/hr and recycled to the carbonylation zone through a line (211), and a medium component consisting of acetic acid was recycled to the carbonylation zone (200) through line (211) and (212) at a rate of 300 parts/hr. A high-boiling component or acetic anhydride that was obtained by fractional distillation was fed to an ED synthesis zone (300) at a rate of about 3641 parts/hr through a line (213). The zone (300) was composed of a reactor equipped with a stirrer and was operated at 70° C.

The crude acetaldehyde stream comprising dimethylacetal, methanol and acetaldehyde was supplied to the ED synthesis zone through a line (114) at a rate of 340 parts/hr together with a recycling stream supplied through a line (411) that consisted of 56 parts/hr of recycled acetaldehyde, about 172 parts/hr of Ed and about 3261 parts/hr of acetic anhydride. In order to maintain the content of benzensulfonic acid in the working fluid at about 3.3 wt %, fresh benzensulfonic acid was added to the working fluid recycled from the ED synthesis zone (300) to the decomposition zone (400), if necessary. The effluent from the ED synthesis zone, or a mixture consisting of methyl acetate (ca. 56 parts/hr), acetic acid (ca. 8 parts/hr), ED (ca. 560 parts/hr) and acetic anhydride (ca. 3205 parts/hr) was supplied through a line (301) to the decomposition zone (400) that was composed of a reactor held at 135° C. and equipped with a stirrer. A mixture from the decomposition zone through lines (403) and (415) that consisted of acetaldehyde (ca. 56 parts/hr), vinyl acetrate (ca. 332 parts/hr), acetic acid (ca. 340 parts/hr), acetic anhydride (ca. 326 parts/hr) and ED (ca. 172 parts/hr) was supplied to the separation zone (410). In the separation zone, acetaldehyde was obtained as a light component at about 2.6 atm. and at 45° C., and was recycled to the ED synthesis zone (300) through the line (411). Vinyl acetate, acetic acid and methyl acetate were separated at 1-3 atm. and at 40°-160° C.; acetic acid was distilled off through a line (414) at a rate of about 340 parts/hr, vinyl acetate distilled off through a line (412) at a rate of about 332 parts/hr, and methyl acetate was supplied to the carbonylation zone (200) through a line (413) at a rate of about 56 parts/hr.

213 Parts/hr of the acetic acid distilled off was esterified with methanol to methyl acetate which was fed to the carbonylation zone (200) through the line (202) as an additional supply.

EXAMPLE 4

The precedure of Example 3 was repeated except that about 340 parts/hr distilled off through line (414) is recovered as a product as it is, and about 332 parts/hr of vinyl acetate distilled off through line (412) was converted to PVA via vinyl acetate polymer, and part of methyl acetate formed as a by-product in the production of PVA, that is about 213 part of methyl acetate was fed into carbonylation zone (200) through line (202). The same results as those of Example 3 was obtained.

What is claimed is:

1. A process for producing vinyl acetate from methanol, carbon monoxide and hydrogen which comprises the following five steps:
   (a) methanol is hydrocarbonylated in a hydrocarbonylation zone to produce ethanol, acetaldehyde, methyl acetate and dimethylacetal in the presence of a catalyst consisting essentially of (i) at least one member selected from the group consisting of metals belonging to Group VIII of the Periodic Table and compounds of the metals as a primary component and (ii) at least one halide as a secondary component, said primary component being used in an amount within the range of from $10^{-6}$ to 0.5 moles per liter of the reaction of metal atom and said secondary component being used in an amount within the range of from $10^{-5}$ to 0.005 moles per liter of the reaction medium in terms of halogen atom, and the products are separated in a separation zone;
   (b) methyl acetate is carbonylated in a carbonylation zone to produce acetic anhydride;
   (c) the acetaldehyde and dimethylacetal produced in step (a) and the acetic anhydride produced in step (b) are converted to ethylidene diacetate and methyl acetate in the presence of at least one acid catalyst selected from the group consisting of Bronsted acids and Lewis acids, the molar ratio of said acetic anhydride to said acetaldehyde plus dimethylacetal being within the range of from 5 to 60;
   (d) the ethylidene diacetate produced in step (c) is thermally decomposed at a temperature between 50° and 200° C. to vinyl acetate and acetic acid, and the products are separated in a separation zone; and
   (e) the methyl acetate produced and separated in steps (a) or (c) is supplied to the carbonylation step (b).

2. Process according to claim 1 wherein the step (c) and (d) are combined into one step wherein the acetaldehyde and dimethylacetal produced in the step (a) and the acetic anhydride produced in the step (b) are directly converted to vinyl acetate, acetic acid and methyl acetate, and the products are separated in a separation zone.

3. The process according to claim 1 which includes a step wherein the acetic acid produced in the step (d) and methanol are converted to methyl acetate.

4. The process according to claim 1 wherein methyl acetate formed as a by-product in the production of PVA is used as part of the starting material.

5. The process according to claim 1 wherein an organic accelerator is used in combination with the catalyst system.

6. The process according to claim 1 wherein the step (b) is carried out in the presence of a catalyst composed of at least one metal component and at least one halide component.

7. The process according to claim 1 wherein the step (b) is carried out at a temperature between 40° and 450° C.

8. The process according to claim 1 wherein the step (d) is carried out at a pressure less than 15 atm.

* * * * *